United States Patent
Li et al.

(10) Patent No.: US 8,057,397 B2
(45) Date of Patent: *Nov. 15, 2011

(54) NAVIGATION AND IMAGING SYSTEM SYCHRONIZED WITH RESPIRATORY AND/OR CARDIAC ACTIVITY

(75) Inventors: Dun Alex Li, Salem, NH (US); Christopher Allen Nafis, Rexford, NY (US); Douglas Glenn Wildes, Ballston Lake, NY (US); Vernon Thomas Jensen, Draper, UT (US); Weston Blaine Griffin, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 905 days.

This patent is subject to a terminal disclaimer.

(21) Appl. No.: 11/863,656

(22) Filed: Sep. 28, 2007

(65) Prior Publication Data
US 2008/0287778 A1 Nov. 20, 2008

Related U.S. Application Data

(60) Provisional application No. 60/938,356, filed on May 16, 2007.

(51) Int. Cl.
*A61B 8/14* (2006.01)
(52) U.S. Cl. ......... 600/467; 600/424; 600/443; 600/450
(58) Field of Classification Search .............. 600/424, 600/437, 443, 450, 462, 467, 471
See application file for complete search history.

(56) References Cited

U.S. PATENT DOCUMENTS

| 6,233,476 | B1 | 5/2001 | Strommer et al. |
| 6,669,635 | B2 | 12/2003 | Kessman et al. |
| 6,716,166 | B2 | 4/2004 | Govari |
| 6,773,402 | B2 | 8/2004 | Govari et al. |
| 7,090,639 | B2 | 8/2006 | Govari |

(Continued)

FOREIGN PATENT DOCUMENTS
EP 1057455 12/2000

OTHER PUBLICATIONS

Proulx, T.L. et al, "Advances in Catheter-Based Ultrasound Imaging", IEEE International Ultrasonics Symposium Proceedings, 2005.

(Continued)

*Primary Examiner* — Brian Casler
*Assistant Examiner* — Amanda Lauritzen
(74) *Attorney, Agent, or Firm* — Andrus, Sceales, Starke & Sawall, LLP

(57) ABSTRACT

An imaging and navigation system is disclosed herein. The imaging and navigation system includes a computer and an ultrasonic imaging device disposed at least partially within an ultrasound catheter. The ultrasonic imaging device is connected to the computer and is adapted to obtain a generally real time three-dimensional image. The imaging and navigation system also includes a tracking system connected to the computer. The tracking system is adapted to estimate a position of a medical instrument. The imaging and navigation system also includes a display connected to the computer. The display is adapted to depict the generally real time three-dimensional image from the ultrasonic imaging device and to graphically convey the estimated position of the medical instrument.

16 Claims, 2 Drawing Sheets

U.S. PATENT DOCUMENTS

| | | | |
|---|---|---|---|
| 7,156,816 | B2 | 1/2007 | Schwartz et al. |
| 2001/0031919 | A1 | 10/2001 | Strommer et al. |
| 2002/0005719 | A1 | 1/2002 | Gilboa et al. |
| 2002/0026118 | A1* | 2/2002 | Govari ............ 600/462 |
| 2002/0042571 | A1 | 4/2002 | Gilboa et al. |
| 2003/0013958 | A1 | 1/2003 | Govari et al. |
| 2003/0074011 | A1 | 4/2003 | Gilboa et al. |
| 2003/0208102 | A1 | 11/2003 | Gilboa |
| 2003/0208123 | A1* | 11/2003 | Panescu ............ 600/431 |
| 2003/0231789 | A1 | 12/2003 | Willis et al. |
| 2004/0097805 | A1 | 5/2004 | Verard et al. |
| 2004/0102769 | A1 | 5/2004 | Schwartz et al. |
| 2004/0138548 | A1 | 7/2004 | Strommer et al. |
| 2004/0162507 | A1 | 8/2004 | Govari |
| 2004/0162550 | A1 | 8/2004 | Govari et al. |
| 2004/0254458 | A1 | 12/2004 | Govari |
| 2005/0197557 | A1 | 9/2005 | Strommer et al. |
| 2006/0241445 | A1 | 10/2006 | Altmann et al. |
| 2006/0253024 | A1 | 11/2006 | Altmann et al. |
| 2006/0253029 | A1 | 11/2006 | Altmann et al. |
| 2006/0253030 | A1 | 11/2006 | Altmann et al. |
| 2006/0253031 | A1 | 11/2006 | Altmann et al. |
| 2006/0253032 | A1 | 11/2006 | Altmann et al. |
| 2007/0073135 | A1* | 3/2007 | Lee et al. ............ 600/407 |
| 2007/0106147 | A1 | 5/2007 | Altmann et al. |
| 2007/0167801 | A1 | 7/2007 | Webler et al. |
| 2007/0167821 | A1 | 7/2007 | Lee et al. |
| 2007/0225593 | A1 | 9/2007 | Porath et al. |

OTHER PUBLICATIONS

Martin, R. et al, "A Miniature Position and Orientation Locator for Three Dimensional Echocardiography", IEEE Proceedings on Computer in Cardiology, pp. 25-28, 1993.

Beaseley, R. A. et al, "Registration of ultrasound images", www.tgt.vanderbilt.edu/archive/Registration of ultrasound images.pdf.

Rotger, D. et al, "Multimodal Registration of Intravascular ultrasound Images and Angiography", Computer Vision Center Universitat Autonoma de Barcelona Bellaterra, Spain, www.cvc.uab.es/~petia/caseib2002.pdf.

Huang, X. et al, "Dynamic 3D Ultrasound and MR Image Registration of the Beating Heart", MICAI, LNCS 3750, pp. 171-178, 2005.

Leotta, D. F. et al, "Three-Dimensional Ultrasound Imaging Using Multiple Magnetic Tracking Systems and Miniature Magnetic Sensors", IEEE on Ultrasonics Symposium, pp. 1415-1418, 1995.

Pagoulatos, N. et al, "Interactive 3-D Registration of Ultrasound and Magnetic Resonance Images Based on a Magnetic Position Sensor", IEE on Info. Tech. In Biomedicine, vol. 3, No. 4, 1999.

\* cited by examiner

NAVIGATION AND IMAGING SYSTEM SYCHRONIZED WITH RESPIRATORY AND/OR CARDIAC ACTIVITY

RELATED APPLICATIONS

This application claims priority to Provisional Application No. 60/938,356 filed on May 16, 2007, and is hereby incorporated herein by reference in its entirety.

BACKGROUND OF THE INVENTION

The subject matter disclosed herein relates to an imaging and navigation system.

Atrial fibrillation is characterized by very rapid uncoordinated electrical signals in the atria of the heart resulting in a rapid and irregular heart beat. Atrial fibrillation can significantly impact a patient's quality of life producing symptoms such as shortness of breath, weakness, difficulty exercising, sweating, dizziness, and fainting. In some patients, atrial fibrillation can be associated with increased risk of stroke, heart failure, or heart muscle disease. It is known to treat atrial fibrillation using a process referred to as cardiac ablation wherein a small section of heart tissue is killed or otherwise rendered inactive thereby breaking the electrical pathways causing the fibrillation.

One problem with interventional procedures such as cardiac ablation is that it is difficult to precisely direct treatment to targeted anatomic regions without damaging surrounding tissue. Another problem with these procedures is that it is difficult to visualize and access appropriate anatomic regions in a minimally invasive manner such that the risk of complications and patient recovery time are minimized.

BRIEF DESCRIPTION OF THE INVENTION

The above-mentioned shortcomings, disadvantages and problems are addressed herein which will be understood by reading and understanding the following specification.

In an embodiment, an imaging and navigation system includes a computer and an ultrasonic imaging device disposed at least partially within an ultrasound catheter. The ultrasonic imaging device is connected to the computer and is adapted to obtain a generally real time three-dimensional image. The imaging and navigation system also includes a tracking system connected to the computer. The tracking system is adapted to estimate a position of a medical instrument. The imaging and navigation system also includes a display connected to the computer. The display is adapted to depict the generally real time three-dimensional image from the ultrasonic imaging device and to graphically convey the estimated position of the medical instrument.

In another embodiment, an imaging and navigation system includes a computer and an ultrasound catheter connected to the computer. The ultrasound catheter is adapted to obtain a generally real time three-dimensional image. The ultrasound catheter system includes a transducer array disposed at least partially within a catheter housing, and a controller coupled with the transducer array. The controller is configured to control the transducer array in order to image a three-dimensional volume. The imaging and navigation system also includes an ablation control system connected to the computer and to an ablation catheter, and a tracking system connected to the computer. The tracking system is adapted to estimate a position of the ablation catheter. The imaging and navigation system also includes a display connected to the computer. The display is adapted to depict the generally real time three-dimensional image from the ultrasound catheter and to graphically convey the estimated position of the ablation catheter.

In another embodiment, an imaging and navigation system includes a computer and an ICE catheter connected to the computer. The ICE catheter is adapted to obtain a generally real time three-dimensional image. The ICE catheter includes a transducer array disposed at least partially within a catheter housing, and a motor coupled with the transducer array. The motor is configured to rotate the transducer array within the catheter housing in order to image a three-dimensional volume. The imaging and navigation system also includes an ablation control system connected to the computer and to an ablation catheter, and a tracking system connected to the computer. The tracking system is adapted to estimate a position and orientation of the ablation catheter. The imaging and navigation system also includes a display connected to the computer. The display is adapted to depict the generally real time three-dimensional image from the ICE catheter and to graphically convey the estimated position and orientation of the ablation catheter.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
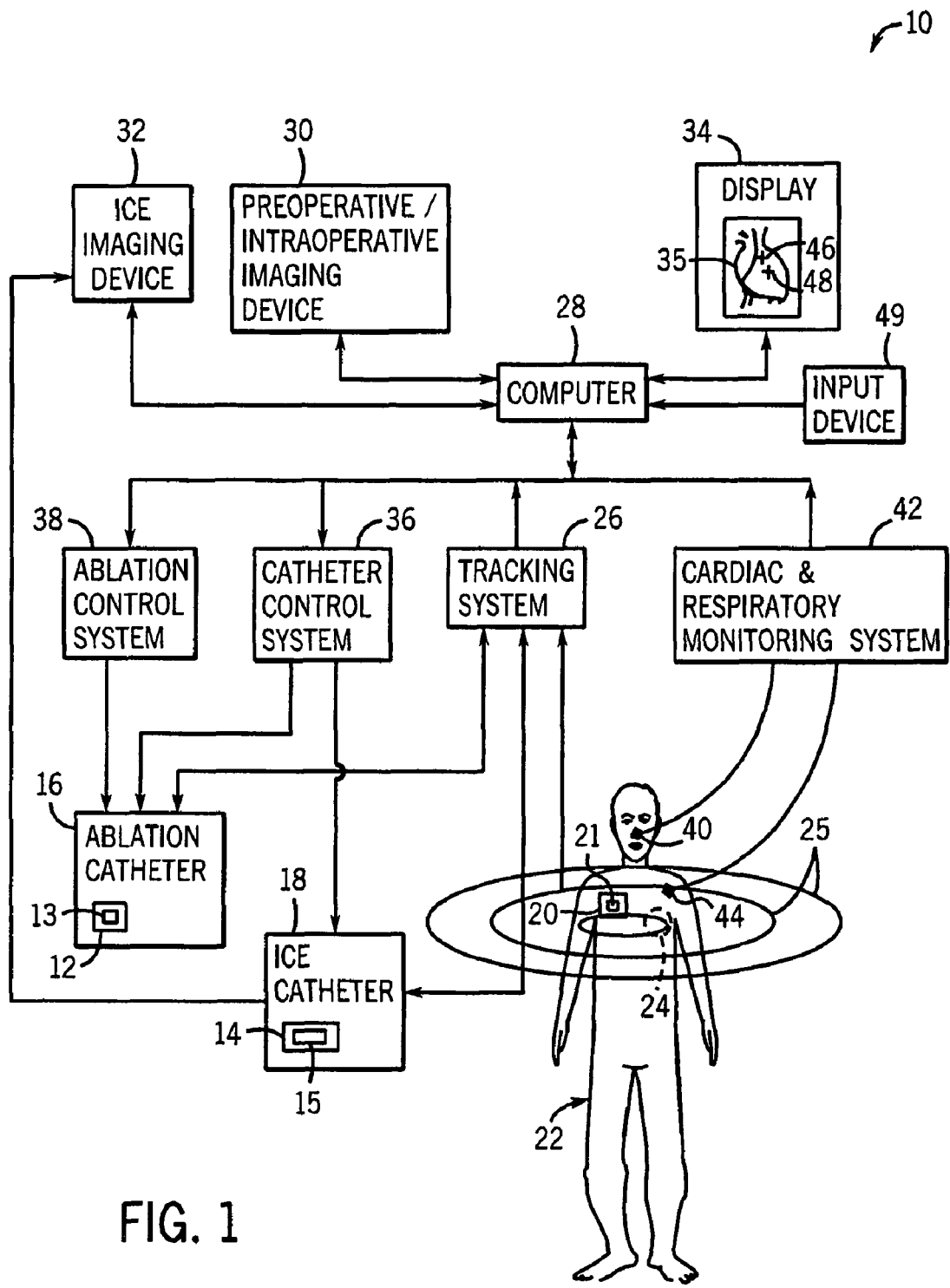
FIG. 1 is a schematic representation of an imaging and navigation system in accordance with an embodiment.

Referring to FIG. 1, a system 10 is shown in accordance with one embodiment. The system 10 will hereinafter be described as an imaging and navigation system adapted for treating atrial fibrillation using an ablation procedure. The system 10 will also hereinafter be described as implementing intracardiac echocardiography (ICE) to facilitate the performance of the ablation procedure. It should, however, be appreciated that the system 10 may also be implemented to treat other medical conditions and to perform other procedures, and that the system 10 may implement alternate ultrasonic technologies in place of ICE.

The navigation portion of the imaging and navigation system 10 includes a tracking system 26 that is operatively connected to a plurality of tracking elements 12, 14 and 20. According to one embodiment, the tracking system 26 and tracking elements 12, 14 and 20 implement electromagnetic (EM) tracking technology, however, alternate tracking technologies and/or tracking systems may be envisioned. The tracking element 12 is adapted for attachment to an ablation catheter 16, and the tracking element 14 is adapted for attachment to an ICE catheter 18. For purposes of this disclosure, a catheter is defined to include any flexible medical delivery system such as, for example, an endoscope. The tracking element 20 can be rigidly attached to an internal organ (e.g., the heart 24) or to the external body of the patient 22 in a conventional manner. A tracking element 20 secured to the patient's heart 24 may be referred to as a "dynamic reference" because it is adapted to move along with the heart 24. An exemplary method of attaching the tracking element 20 to the patient's heart 24 is through a minimally invasive procedure using a dynamic reference catheter (not shown).

The present invention will hereinafter be described in accordance with an embodiment wherein the tracking element 20 comprises a field generator 21, the tracking element 12 comprises one or more field sensors 13, and the tracking element 14 comprises one or more field sensors 15. It should, however, be appreciated that according to alternate embodiments the tracking element 20 may include a field sensor and the tracking elements 12, 14 may include field generators. The field generator 21 generates a magnetic field 25 in an area that includes the target site (e.g., the patient's heart 24). The field sensors 13, 15 are adapted to measure the magnetic field 25, and to transmit the magnetic field measurements to the tracking system 26. The tracking system 26 implements the magnetic field measurements to calculate the position and orientation of the tracking elements 12, 14. After calculating the position and orientation of the tracking elements 12, 14, the position and orientation of the ablation catheter 16 and the ICE catheter 18 respectively attached thereto can also be calculated in a known manner.

The tracking system 26 transmits the catheter position and orientation data to a computer 28. The computer 28 registers the position and orientation data to an image obtained from a preoperative/intraoperative imaging device 30 and/or to an image obtained from an ICE imaging device 32. The preoperative/intraoperative imaging system 30 may, for example, include a CT imaging device, a MR imaging device, a PET imaging device, an ultrasound imaging device, an X-ray imaging device, or any other known imaging device, as well as any combinations thereof. The preoperative/intraoperative imaging device 30 may provide 2D, 3D or 4D images. For purposes of this disclosure, 4D refers to the three primary dimensions (i.e., as measured along X, Y and Z axes) and the fourth dimension which is time. Therefore, for purposes of this disclosure, 4D is synonymous with generally real time 3D. Also for purposes of this disclosure, a generally real time image includes a maximum image delay of approximately one second. The ICE imaging device 32 is configured to obtain imaging data from the ICE catheter 18 and produce 2D, 3D or 4D images as will be described in detail hereinafter.

The catheter position and orientation data can be visualized on the display 34. According to one embodiment, graphic representations corresponding to the ablation catheter 16 and the ICE catheter 18 may be virtually superimposed on a patient image obtained from the preoperative/intraoperative imaging device 30 and/or the ICE imaging device 32. In the embodiment of FIG. 1, the graphic representations include the cross-hairs 46, 48 respectively representing the distal end portions of the ablation catheter 16 and the ICE catheter 18, however other embodiments may include a more complete rendering showing the catheters 16, 18 in detail.

The input device 49 may include any known apparatus or system such as a keyboard, mouse, touch screen, joystick, etc., and is generally adapted to allow a user to manually input data into the system 10. Although shown in FIG. 1 as a separate component, the input device 49 may alternatively be incorporated into one of the other system 10 components such as the computer 28 or the display 34. As an example, the input device 49 may include a touch screen device integrated into the design of the display 34 and adapted to facilitate surgical planning. According to one embodiment, the exemplary touch screen input device 49 could be implemented to highlight or otherwise identify specific regions of interest on a patient image obtained from one of the imaging devices 30, 32. According to another embodiment, the exemplary touch screen input device 49 could be implemented to assign a priority sequence to a plurality of regions of interest.

A catheter control system 36 is operatively connected to both the ablation catheter 16 and the ICE catheter 18. The catheter control system 36 is adapted to translate and steer the catheters 16, 18 through the patient 22 to a predefined destination at or near the patient's heart 24. The catheter control system 36 may be configured to translate and steer the catheters 16, 18 in response to manual operator inputs, or may be configured to automatically direct the catheters 16, 18 to a selectable target site. The catheter control system 36 may also be operatively connected to and configured to control a dynamic reference catheter (not shown) adapted to facilitate the attachment of the tracking element 20 to the patient's heart 24.

An ablation control system 38 controls the energy transfer to the ablation catheter 16. Accordingly, when an operator determines that the distal end of the ablation catheter 16 is in sufficiently close proximity to a targeted cardiac region, the ablation control system 38 can be implemented to transmit a selectable amount of energy. The transmission of energy in this manner kills or otherwise renders inactive the targeted region in order to break electrical pathways causing atrial fibrillation. In a non-limiting manner, the ablation control system 38 may implement radio frequency (RF), cryogenic, ultrasound, or laser technologies.

One or more respiratory sensors 40 can be positioned near the patient's mouth and/or nose in order to monitor respiration, and one or more cardiac sensors 44 can be positioned near the patient's heart 24 to monitor cardiac activity. The respiratory sensors 40 and the cardiac sensors 44 are operatively associated with and adapted to transmit sensor data to a monitoring system 42. Any sensor data collected by the monitoring system 42 is transferable to the computer 28 such that the computer 28 may be implemented to synchronize the operation of the tracking system 26, the imaging device 30, and/or the imaging device 32 with the patient's cardiac and respiratory activity. According to one example, the computer 28 may implement data from the monitoring system 42 to acquire images during predefined portions of a patient's cardiac or respiratory cycle. According to another example, the computer 28 may implement data from the monitoring system 42 to sequence a series of 2D images or slices in a manner that corresponds with a patient's cardiac or respiratory cycle in order to provide a generally real time rendering of a dynamic object such as the patient's heart 24.

Figure 2:
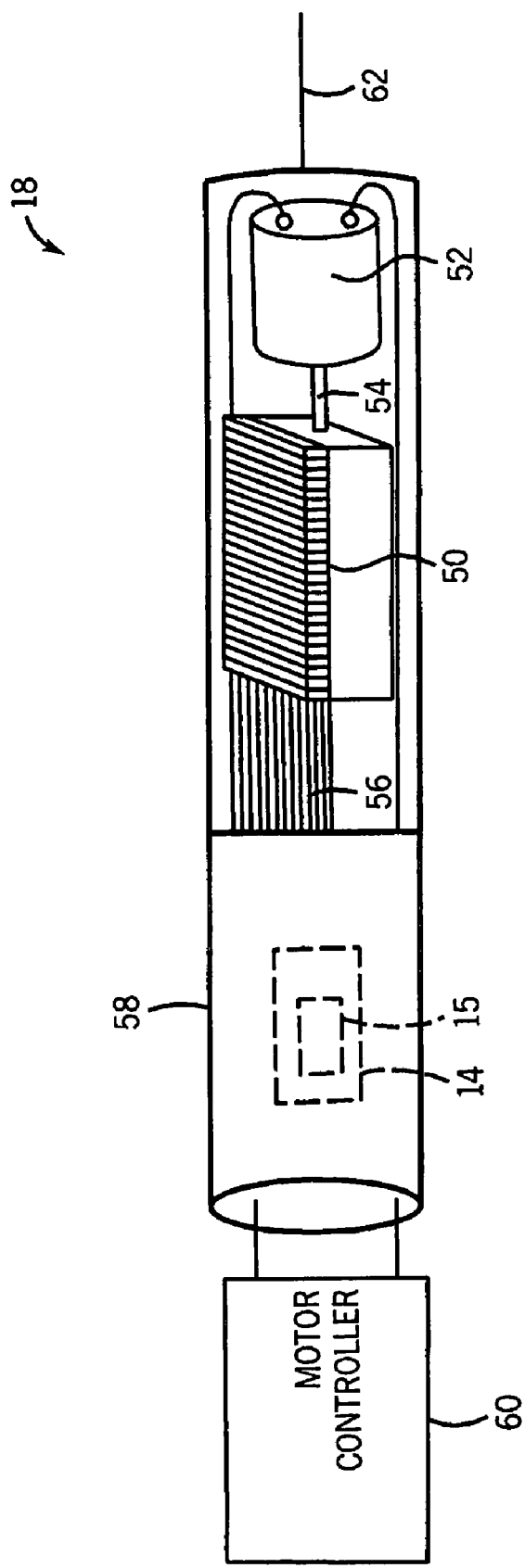
FIG. 2 is a partially cutaway schematic illustration of an ICE catheter in accordance with an embodiment.

Referring to FIG. 2, a more detailed illustration of the ICE catheter 18 is shown. The ICE catheter 18 will hereinafter be described in detail in accordance with an embodiment. It should, however, be appreciated that the ICE catheter 18 may be replaced with a similar catheter system adapted to retain any known ultrasonic imaging device.

The ICE catheter 18 comprises a transducer array 50, a motor 52, which may be internal or external to the space-critical environment, a drive shaft 54 or other mechanical connections between motor 52 and the transducer array 50, and an interconnect 56. The ICE catheter 18 further includes a catheter housing 58 enclosing the transducer array 50, motor 52, interconnect 56 and drive shaft 54. In the depicted embodiment, the transducer array 50 is mounted on drive shaft 54 and the transducer array 50 is rotatable with the drive shaft 54. The rotational motion of the transducer array 50 is controlled by motor controller 60 and motor 52. Interconnect 56 refers to, for example, cables and other connections coupling the transducer array 50 with the ICE imaging device 32 (shown in FIG. 1) for use in receiving and/or transmitting signals therebetween. In an embodiment, interconnect 56 is configured to reduce its respective torque load on the transducer array 50 and motor 52. The catheter housing 58 is of a material, size and shape adaptable for internal imaging applications and insertion into regions of interest. According to the embodiment depicted in FIG. 2, the catheter housing 58 is generally cylindrical defining a longitudinal axis 62.

The catheter housing 58, or at least the portion that intersects the ultrasound imaging volume, is acoustically transparent, e.g. low attenuation and scattering, acoustic impedance near that of blood and tissue (Z~1.5M Rayl). The space between the transducer and the housing can be filled with an acoustic coupling fluid (not shown), e.g., water, with acoustic impedance and sound velocity near those of blood and tissue (Z~1.5 M Rayl, V~1540 m/sec).

According to one embodiment, the transducer array 50 is a 64-element one-dimensional array having 0.110 mm azimuth pitch, 2.5 mm elevation and 6.5 MHz center frequency. The elements of the transducer array 50 are electronically phased in order to acquire a sector image parallel to the longitudinal axis 62 of the catheter housing 58. The transducer array 58 is mechanically rotated about the longitudinal axis 62 to image a three-dimensional volume. The transducer array 50 captures a plurality of two-dimensional images as it is being rotated. The plurality of two-dimensional images are transmitted to the ICE imaging device 32 (shown in FIG. 1) which is configured to sequentially assemble the two-dimensional images in order to produce a three-dimensional image.

The rate at which the transducer array 50 is rotated about the longitudinal axis 62 can be regulated by the motor controller 60. The transducer array 50 can be rotated relatively slowly to produce a 3D image, or relatively quickly to produce a generally real time 3D image (i.e., a 4D image). The motor controller 60 is also operable to vary the direction of rotation to produce an oscillatory transducer array motion. In this manner, the range of motion and imaged volume are restricted such that the transducer array 50 can focus on imaging a specific region and can update the 3D image of that region more frequently, thereby providing a generally real time 3D, or 4D, image.

Referring to FIGS. 1 and 2, an embodiment of the ICE catheter 18 includes an integrally attached tracking element 14 disposed within the catheter housing 58. The integrally attached tracking element 14 is adapted to work in combination with the tracking element 20 and the tracking system 26 to estimate the position and/or orientation of the ICE catheter 18. As previously described, the tracking element 14 may comprise either the field sensor 15 or a field generator (not shown) similar to the field generator 21.

It should be appreciated by those skilled in the art that the previously described ICE catheter 18 is a single embodiment, and that alternate configurations may be envisioned. For example, the transducer array 50, motor 52 and drive shaft 54 define a mechanical 4D ICE embodiment that could be replaced by a functionally equivalent electrical 4D ICE embodiment (not shown). The electrical 4D ICE embodiment may, for example, comprise a 2D matrix transducer array (not shown) integrated with an electronic device (not shown) configured to steer the ultrasound beam in azimuth and elevation. In this manner, the electrical 4D ICE embodiment could image a 3D or 4D volume without necessarily moving the transducer array.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

We claim:
1. An imaging and navigation system comprising:
 a computer;
 an ultrasonic imaging device disposed at least partially within an ultrasound catheter, the ultrasonic imaging device connected to the computer, the ultrasonic imaging device being adapted to obtain a generally real time three-dimensional image;
 a tracking system connected to the computer, the tracking system adapted to estimate a position of a medical instrument;
 a first tracking element connected to the tracking system and configured for attachment to the ultrasound catheter;
 a second tracking element connected to the tracking system and configured for attachment to a dynamic reference catheter;
 a monitoring system connected to the computer, the monitoring system configured to monitor respiratory and/or cardiac activity;
 a display connected to the computer, the display adapted to depict the generally real time three-dimensional image from the ultrasonic imaging device and to graphically convey the estimated position of the medical instrument;
 wherein the computer is configured to synchronize the operation of the ultrasonic imaging device with the respiratory and/or cardiac activity.

2. The imaging and navigation system of claim 1, wherein the ultrasound catheter comprises:
 a transducer array disposed at least partially within a catheter housing; and
 a motor coupled with the transducer array, the motor being configured to rotate the transducer array within the catheter housing in order to image a three-dimensional volume.

3. The imaging and navigation system of claim 1, wherein the computer is configured to synchronize the operation of the tracking system with the respiratory and/or cardiac activity.

4. The imaging and navigation system of claim 1, wherein one of the tracking elements comprises a field generator, and the other of the tracking elements comprises a field sensor.

5. The imaging and navigation system of claim 1, further comprising a catheter control system connected to the computer and to the ultrasound catheter.

6. The imaging and navigation system of claim 1, further comprising an input device operatively associated with the display, the input device being adapted to facilitate surgical planning.

7. An imaging and navigation system comprising:
 a computer;
 an ultrasound catheter connected to the computer, the ultrasound catheter being configured to obtain a generally real time three-dimensional image, the ultrasound catheter system comprising:
 (a) a transducer array disposed at least partially within a catheter housing;

(b) a controller coupled with the transducer array, the controller being configured to control the transducer array in order to image a three-dimensional volume;

an ablation control system connected to the computer and to an ablation catheter;

a tracking system connected to the computer, the tracking system configured to estimate a position of the ablation catheter;

a first tracking element connected to the tracking system and configured for attachment to the ultrasound catheter;

a second tracking element connected to the tracking system and adapted for attachment to the ablation catheter;

a monitoring system connected to the computer, the monitoring system configured to monitor respiratory and/or cardiac activity; and a display connected to the computer, the display configured to depict the generally real time three-dimensional image from the ultrasound catheter and to graphically convey the estimated position of the ablation catheter;

wherein the computer is configured to synchronize the operation of the tracking system with the respiratory and/or cardiac activity.

8. The imaging and navigation system of claim 7, wherein the computer is configured to synchronize the operation of the ultrasound catheter with the respiratory and/or cardiac activity.

9. The imaging and navigation system of claim 7, further comprising a third tracking element connected to the tracking system and configured for attachment to a dynamic reference catheter.

10. The imaging and navigation system of claim 7, further comprising a catheter control system connected to the computer, the ultrasound catheter and the ablation catheter.

11. The imaging and navigation system of claim 7, wherein the ultrasound catheter comprises an intracardiac echocardiography (ICE) catheter.

12. An imaging and navigation system comprising:

a computer;

an intracardiac echocardiography (ICE) catheter connected to the computer, the ICE catheter comprising:

(a) a transducer array disposed at least partially within a catheter housing;

(b) a motor coupled with the transducer array, the motor being configured to rotate the transducer array within the catheter housing in order to obtain a three-dimensional volume;

an ablation control system connected to the computer and to an ablation catheter;

a tracking system connected to the computer the tracking system configured to estimate a position and orientation of the ablation catheter;

a first tracking element connected to the tracking system and configured for attachment to the ICE catheter;

a second tracking element connected to the tracking system and configured for attachment to the ablation catheter;

a monitoring system connected to the computer, the monitoring system configured to monitor the respiratory and/or cardiac activity;

a display connected to the computer, the display configured to depict the generally real time three-dimensional image from the ICE catheter and to graphically convey the estimated position and orientation of the ablation catheter;

wherein the computer is configured to synchronize the operation of the ICE catheter with the respiratory and/or cardiac activity.

13. The imaging and navigation system of claim 12, wherein the computer is configured to synchronize the operation of the tracking system with the respiratory and/or cardiac activity.

14. The imaging and navigation system of claim 13, further comprising a third tracking element connected to the tracking system and configured for attachment to a dynamic reference catheter.

15. The imaging and navigation system of claim 14, wherein one of the tracking elements comprises a field generator, and another of the tracking elements comprises a field sensor.

16. The imaging and navigation system of claim 15, further comprising an input device operatively associated with the display, the input device being adapted to facilitate surgical planning.

* * * * *